United States Patent [19]

Sachinvala

[11] Patent Number: 5,166,334
[45] Date of Patent: Nov. 24, 1992

[54] 1',2,3,3',4,4'-HEXA-O-METHYLSUCROSE

[75] Inventor: Navzer D. Sachinvala, Aiea, Hi.

[73] Assignee: Hawaiian Sugar Planter's Ass., Hi.

[21] Appl. No.: 623,523

[22] Filed: Dec. 7, 1990

[51] Int. Cl.$^5$ .................. C07H 15/04; C07H 3/04; C07H 1/00

[52] U.S. Cl. .................. 536/124; 536/120; 536/18.2; 536/122

[58] Field of Search .............. 536/120, 115, 116, 119, 536/124

[56] References Cited

U.S. PATENT DOCUMENTS

| 4,156,776 | 5/1979 | Mufti et al. | 536/120 |
| 4,378,369 | 3/1983 | Simpson | 514/473 |

OTHER PUBLICATIONS

Dirlikov, "Monomers and Polymers based on Mono- and Dissaccharides", Pacific Polymer Preprints, vol. 1 (Nov. 1989), pp. 113–114.

Hough et al. "Sucrochemistry. Part II. 6,6'-Di-O-tritylsucrose", Carbohyd. Res., vol. 21 (1972), pp. 144–147.

O'Donnell et al., "Synthesis fo Some Partially Methylated Sucrose Derivatives", Aust. J. Chem., vol. 25 (1972), pp. 407–412.

Ogata et al., "Molecular Weight Control in Polycondensation of Hydroxyl Diesters with Hexamethylenediamine by Polymer Matrices", Journal of Polymer Science: Polymer Chemistry Edition, vol. 19 (1981), pp. 2609–2617.

Dirlikov, "Monomes and Polymers based on Mono–and Disaccharides", Pacific Polymer Preprints, vol. 1, (Dec. 12–15, 1989), pp. 113–114.

Primary Examiner—Johnnie R. Brown
Assistant Examiner—Everett White

[57] ABSTRACT

A 1', 2,3,3',4,4'-hexa-O-methylsucrose compound is disclosed which is useful as an intermediate compound to make water-absorbent polyesters and polyethers. This compound may be used as an intermediate and oxidized to a dicarboxylic acid to make other novel polyesters or polyamides.

6 Claims, 11 Drawing Sheets

1′,2,3,3′,4,4′-HEXA-O-METHYLSUCROSE

GRANT REFERENCE

The invention described herein was partially funded by U.S.D.A. (A.R.S.) grant number 58-91H2-0-319.

BACKGROUND OF THE INVENTION

1. Field of the Invention

The present invention relates to a chemical intermediate having the following structure (I):

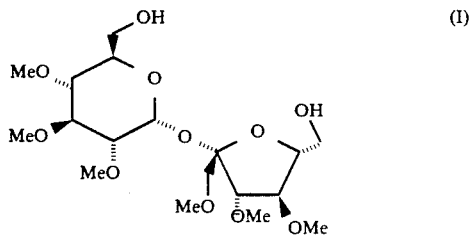

This diol can be used as a monomer for the preparation of water absorbent polyethers and polyesters.

2. Description of the Prior Art

In the past, many attempts have been made to employ carbohydrates for the development of well-characterized novel polymers of some practical significance. The use of sugars and their derivatives in the production of polymers is of growing interest since polymers containing mono- or disaccharides in their main chain or as grafted pendant groups or chains display useful and unique properties such as hydrophilicity, chirality, biological activity, biodegradability, and the like. Furthermore, most sugars are available at economical prices and are industrially produced in large quantities by cultivation in plants and microorganisms, followed by chemical isolation or by degradation of plant waste material followed by isolation. For instance, sucrose is produced on a scale that is larger than any other pure organic chemical, world-wide.

The major problem associated with the use of carbohydrates for developing polymers is the similar reactivity of the primary and secondary hydroxyl groups on the carbohydrate moiety. Hence, when carbohydrates are polymerized non-enzymatically with other monomers, the resulting polymer products are often a mixture of linear, cross-linked and branched chain products. This is due to the reaction of both the primary and secondary hydroxyl groups in the carbohydrate moiety with electrophilic groups in the other monomer.

Many attempts have been made in the past towards polymerizing carbohydrates such as those described by N. Ogata et al in *J. Polym. Sci.*, Polym. Chem. Ed., Vol. 19, p. 2609 (1981) and Vol. 22, p. 739 (1984); and S. K. Dirlikov, "Monomers and Polymers Based on Mono and Disaccharides", Pacific Polymer Preprints, First Pacific Polymer Conference, December 12-15, 1989, Volume 1, pp. 113-114.

Although Dirlikov, supra, claims that high molecular weight polymers have been made, no proof has been shown that these polymers are strictly linear and do not contain additional cross-linked or branched chain polymers and that only the primary hydroxyl groups react thereby forming a strictly linear polymer.

Sucrose used as a starting carbohydrate for the production of carbohydrate polymers would be ideal since it is produced in vast quantities and is low in price. To synthesize intermediate sucrose derivatives for further use in the production of novel polymers using sucrose as a starting compound is difficult due to the reactivity of the primary hydroxyl groups at carbons 6, 1′ and 6′ and the remaining five secondary hydroxyl groups.

For instance, U.S. Pat. No. 4,156,776 describes a 1′,2,3,3′,4′,640-hexa-O-acetylsucrose derivative that is useful as a component of inks, adhesives, coatings and vinyl ethers, but this compound contains acetyl moieties as does the acetoxy derivative of 4,6-O-isopropylidene sucrose a potentially useful synthetic intermediate. The use of acetates as semipermanent protection of secondary hydroxyl groups is often unfeasible since the hydroxyl group at the 6 position undergoes an internal acetate exchange to produce the 6-acetate and an hydroxyl group at the 4-position. In addition when acetates are used to protect secondary alcohols, the acetate protecting groups preclude the use of bases or nucleophiles in their presence.

Protecting the secondary hydroxyl groups in tri-O-trityl sucrose as the methyl ethers followed by reductive cleavage of the trityl groups affords an intermediate 2,3,3′,4,4′-penta-O-methylsucrose. This compound is further manipulated to prepare 1′,2,3,3′,4,4′-hexa-O-methylsucrose as well as many other monomers.

It has now surprisingly been discovered that the diol monomer of 1′,2,3,3′,4,4′-hexa-O-methylsucrose can be synthesized via a two step process from 6,6′-dichloro-6,6′-dideoxy-1′,2,3,3′,4,4′-hexa-O-methylsucrose and that this compound can be used for the preparation of water absorbent polyethers and polyesters.

OBJECTS AND SUMMARY OF THE INVENTION

It is an object of the present invention to avoid or alleviate the problems of the prior art.

It is another object of the present invention to provide a compound of 1′,2,3,3′,4,4′-hexa-O-methylsucrose.

It is yet another object of the present invention to provide a diol monomer of 1′,2,3,3′,4,4′-hexa-O-methylsucrose that can be used to prepare water absorbent polyethers and polyesters.

Basically, the present invention features a compound having the following structure (I):

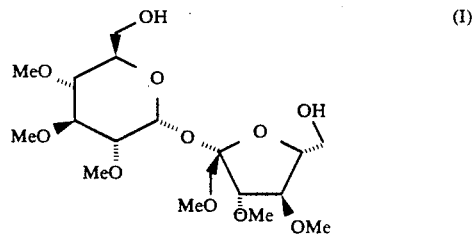

which compound is 1′,2,3,3′,4,4′-hexa-O-methylsucrose.

Another feature of the present invention includes a method of using 1′,2,3,3′,4,4′-hexa-O-methylsucrose to produce a polyamine comprising oxidizing the 6 and 6′-hydroxyl groups of 1′,2,3,3′,4,4′-hexa-O-methylsucrose to 6,6′-dialdehydes and reductive coupling said dialdehydes with an alkyl or aryl diamine at a temperature between 100° C. to 120° C.

Yet another feature of the present invention includes a method of using using 1′,2,3,3′,4,4′-hexa-O-methylsucrose to produce a polyether comprising deprotonating the 6 and 6'-dinydroxy groups or 1',2,3,3',4,4'-hexa-O-methylsucrose with a non-nucleophilic base to form a metal alkoxide and treating said metal alkoxides with an alkyl or benzylic dihalide.

DETAILED DESCRIPTION OF THE PREFERRED EMBODIMENTS OF THE INVENTION

Figure 1:
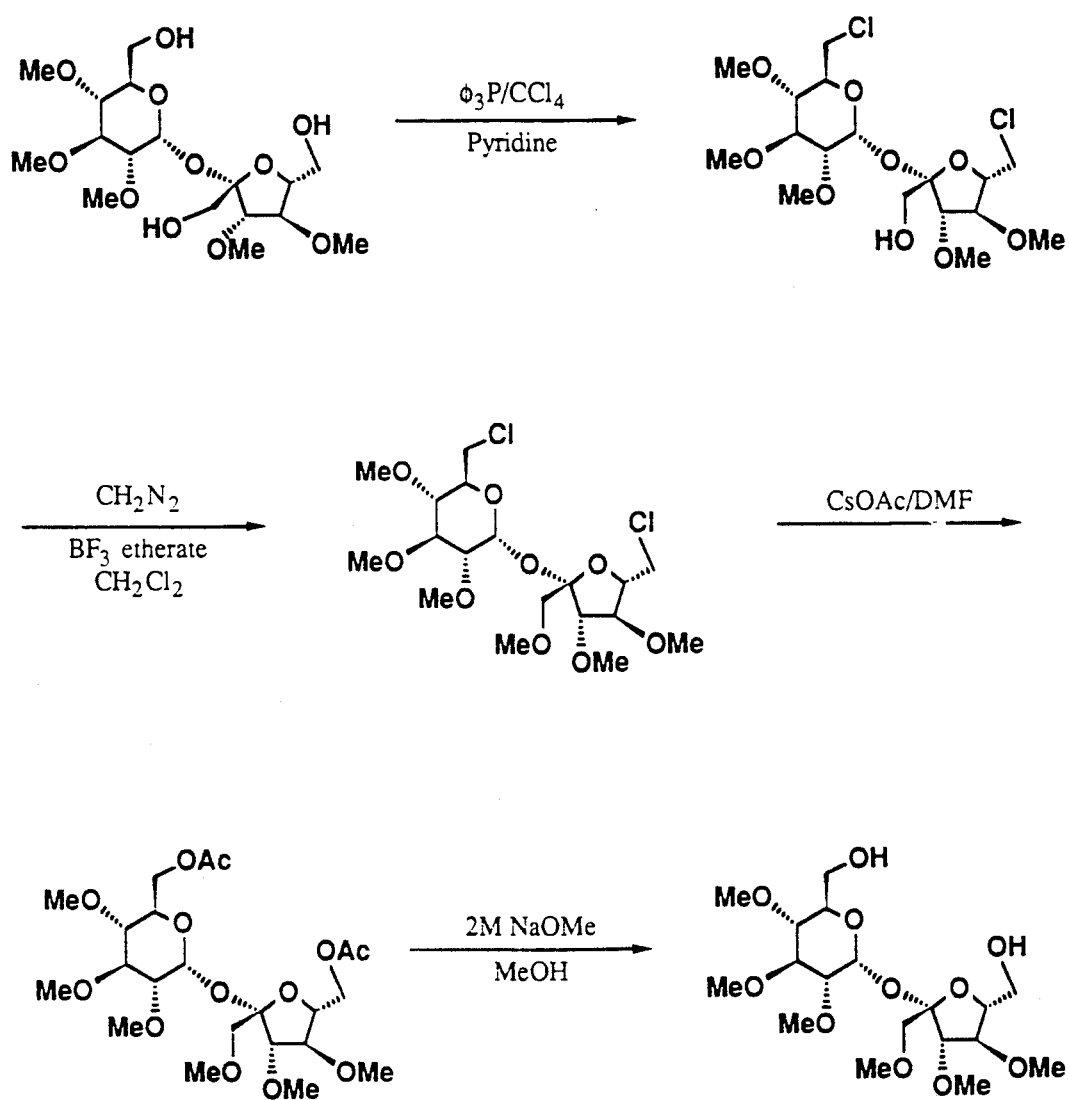
FIG. 1 represents the synthesis scheme of 1',2,3,3',4,4'-hexa-O-methylsucrose.

As described herein, the term "dihalo" means dichloro, dibromo or diiodo and does not include difluoro compounds. Similarly, the terms "dihalide" and "tetrahalomethane" do not include fluorine compounds.

More specifically, the synthesis of the compound of structure (I) can be accomplished via addition of cesium acetate followed by hydrolysis using sodium methoxide in methanol. The synthesis requires the use of 6,6'-dihalo-6,6'-dideoxy-140 ,2,3,3',4,4'-hexa-O-methylsucrose as an intermediate compound.

The starting compound used in the synthesis of the compound encompassing the structure of (I) is 2,3,3',4,4'-penta-O-methylsucrose. 2,3,3',4,4'-Penta-O-methylsucrose is synthesized from sucrose by converting sucrose to 1',6,6'-tri-O-tritylsucrose, which is converted to a penta-methyl ether moiety and reduced with an alkali metal in liquid ammonia to form the final product.

The starting compound, sucrose, is first converted to 1',6,6'-tri-O-tritylsucrose by reacting sucrose with trityl chloride. This method is described by Hough et al in the journal *Carbohydrate Research*, Vol. 21 (1972), pp. 414–417, and is incorporated herein with some modifications. Specifically, the process involves the addition of trityl (triphenylmethyl) moieties to the 1', 6, and 6' positions on the sucrose molecule. The synthesis is performed by adding a solution of trityl chloride in dimethylformamide to a solution of sucrose in dimethylformamide and triethylamine. The amount of sucrose used may vary. For instance, between 314 mg (1 mmol) to 70 grams (204.5 mmol) of sucrose may be used. The amount of trityl chloride may also vary depending on the amount of starting sucrose used. For instance, about 4.5 times the molar amount of trityl chloride is used per mole of sucrose, and, therefore, it is preferable to use 260 grams (935 mmol) of tritylchloride per 70 grams (204.5 mmol) of sucrose. After dropwise addition of a solution of trityl chloride in dimethylformamide at 0° to 5° C. over a time period of about one hour, the mixture is allowed to warm to room temperature and then stirred at a constant temperature of about 45° C. for two days. The mixture is then concentrated to about half the original volume under reduced pressure and dissolved in methylene chloride, washed successively with water, 1M hydrochloric acid, saturated aqueous sodium bicarbonate, water, and brine, and then dried in the presence of sodium sulfate. The methylene chloride is then removed in vacuo. The residue is then applied on a column of silica gel (230 to 400 mesh) and eluted successively with methylene chloride, 10% acetone in methylene chloride and 20% acetone in methylene chloride at a flow rate of about 100 ml/min. 100 ml fractions are collected, and each fraction is spotted on a thin-layer chromatography plate, and the plate is developed with 20% acetone in methylene chloride. Three compounds elute from the column with methylene chloride and 10% acetone in methylene chloride. These three compounds are nonpolar compounds and typically have Rf values of 0.83, 0.74, and 0.62 on silica gel 60 plates (0.25 mm, F-254 E. Merck). The desired 1',6,6'-tri-O-tritylsucrose elutes with 20% acetone in methylene chloride and has an Rf value of 0.21 in 20% acetone in methylene chloride. The yield of 1',6,6'-tri-O-tritylsucrose using this method is typically between 65% and 70%.

The tri-O-tritylsucrose adduct is then O-methylated at positions 2, 3, 3', 4 and 4' to produce 1',6,6'-tri-O-trityl-2,3,3',4,4'-penta-O-methylsucrose. The penta-O-methylation is performed under conditions that take advantage of the fact that a hydride base reacts rapidly with the secondary alcohols to produce hydrogen gas and the said alkoxides without the possibility of reverting back to the alcohols. The alkoxides are then alkylated with an alkylating agent such as methyl iodide or dimethylsulfate to produce the penta-O-methyl ethers.

In the synthesis of the intermediate compound, 1',6,6'-tri-O-trityl-2,3,3',4,4'-penta-O-methylsucrose, all group (I) and group (II) metal hydrides, as well as all group (I) and group (II) bases can be used to convert the secondary alcohols to alkoxides. More specifically, sodium hydride, potassium hydride and the like. It is preferable to use sodium hydride.

Alternatively, lithium bases can also be used. In the case of alkyl lithium bases, a solution of the lithium base is added to the polyhydroxy compound at low temperatures. Specific examples of these bases include methyllithium, butyllithium, t-butyllithium, phenyllithium, sodium hydride, potassium hydride, and the like, to mention only a few. It is preferable to use a hydride base such as sodium hydride in the present process.

The amount of group (I) and group (II) metal hydrides and the aforementioned bases utilized in the second step of this process may vary depending on the amount of 1',6,6'-tri-O-tritylsucrose used in the reaction. For scales up to 10 mmol or 10.69 grams of tri-O- tritylsucrose, approximately 6 grams to 10 grams or 150 mmol to 250 mmol of a 60% dispersion of sodium hydride in oil are used. The presence of 3 to 5 equivalents of hydride base per reactive hydroxyl group in tri-O-tritylsucrose will ensure complete deprotonation of the alcohol to form the alkoxide, without the possibility of reverting back to the alcohol, provided no excess proton source is purposely introduced into the reaction mixture (i.e., by addition of water or other protic solvents). The excess sodium hydride is added to assure that the reaction mixture stays dry in case traces of moisture are accidentally introduced. If greater than 10 mmol of 1',6,6'-tri-O-tritylsucrose is reacted, i.e., 50 grams (46.76 mmol) to 150 grams (140 mmol), then an equal weight in grams of sodium hydride (60% in oil) is used. Thus, for instance, for 150 grams of tri-O-tritylsucrose, 150 grams (3900 mmol) of sodium hydride (60% dispersion in oil) is used. For large scale synthesis, it is preferable to use 5 equivalent excess of hydride ion for each hydroxyl group in tri-O-tritylsucrose.

The hydride is usually stored as a dispersion in oil at varying concentrations. Prior to using the hydride base in the reaction, it should be washed free of the oil with pentane. Then the washed hydride is resuspended in a suitable solvent. Any polar aprotic solvent that can suspend or dissolve the hydride may be used, provided the solvent and hydride do not destructively react at the temperatures needed to deprotonate the alcohols. For example, dimethylformamide (DMF) begins to decompose in the presence of sodium hydride at 55° C. to 60° C. within a few hours to produce carbon monoxide and sodium dimethylamide. Examples of suitable hydrides and their corresponding solvent for this reaction include sodium hydride in DMSO, potassium hydride in DMSO at low temperatures of 0° to 40° C., sodium hydride in tetrahydrofuran (THF), potassium hydride in tetrahydrofuran (THF), sodium hydride in HMPA (hexamethylphosphoric triamide), sodium hydride in N-methylpyrrolidone, potassium hydride in N-methylpyrrolidone, sodium hydride in DMSO/THF, potassium hydride in DMSO/THF at low temperatures of 0° to 40° C., sodium or potassium hydrides in DMF at low temperatures of 0° to 40° C., calcium hydride in hexamethylphosphoric triamide, methyllithium, phenyllithium, butyllithium, sec-butyllithium or t-butyllithium in ether solvents such as tetrahydrofuran (THF), dioxane, dimethoxyoxyethane, diethylether or t-butylmethyl ether, alkyl lithium or aryl lithium and magnesium reagents in hexamethylphosphoric triamide or N-methylpyrrolidone, transition metal salts and hydrides of copper, cadmium, cobalt, and the like. It is preferable to use dimethylsulfoxide (DMSO) for a variety of reasons since methyl protons of DMSO are less acidic than the hydroxyl group protons of tri-O-tritylsucrose, DMSO does not completely react with sodium hydride to form the dimsylanion within 30 to 60 minutes at temperatures ranging between 25° C. to 55° C., and the red penta anion of tri-O-tritylsucrose is very soluble in DMSO. Moreover, since only small amounts of the dimsylanion is formed by using DMSO, the anion will react with the hydroxyl groups in tri-O-tritylsucrose to form alkoxides. The amount of solvent used in the present invention may vary depending upon the amount of tri-O-tritylsucrose and hydride used in the reaction. It is preferable to use 10 ml of DMSO per gram of tri-O-tritylsucrose or 0.1M tri-O-tritylsucrose in DMSO.

The addition of the 1',6,6'-tri-O-tritylsucrose to the hydride base usually takes place at a temperature between 45° C. to 55° C. to permit the formation of alkoxides. It is preferable, however, that the reaction proceed at a temperature of about 50° C. to 60° C., most preferably about 50° C. The internal temperatures do not ever rise above 60° C.

This addition usually takes place over a period of 20 minutes to three hours depending on the amount of starting 1',6,6'-tri-O-tritylsucrose being used. For instance, if up to 10 mmol of the tritylsucrose is being reacted, then the addition takes place over a period of about 30 minutes. If the starting tritylsucrose concentration is greater than 10 mmol, then the addition to the hydride base may take up to 3 hours. The 1',6,6'-tri-O-tritylsucrose is added dropwise under constant stirring while the reaction temperature is monitored by placing a thermometer in the stirring vessel. After the addition of the tritylsucrose, the reaction mixture is maintained at the above-described temperature and constantly stirred for an additional time period. Usually, this period is approximately 90 minutes.

After hydrogen evolution has ceased completely, a burgundy-red solution is obtained. This solution is then cooled to a temperature between 0° C. and 25° C.

Upon cooling the reaction mixture, an alkylating agent is then added dropwise over a varying time period, depending on the amounts of alkylating agents being added. For instance, in preparation containing up to 10 mmol of the tritylsucrose, the alkylating agent may be added over a period of about 30 minutes since less of the alkylating agent is used in the reaction. For preparations of larger than 10 mmol, the alkylating agent may be added over a time span of up to 90 minutes.

Any alkylating agent may be used in the present invention that will add an alkyl moiety to the alkoxide. Examples of the alkylating agents, which may be used in the present invention include methyl iodide, dimethyl sulfate, methyl chloride, methyl bromide, allyl bromide, benzyl bromide, octyl iodide, butyl iodide, halides and sulfonate esters of long chain hydrocarbons, and the like. If methyl iodide is used in this method, then it is usually freshly distilled over copper. The concentration of the alkylating agent may vary depending upon the amount of starting material present in the reaction medium. It is preferable to use a 5 molar equivalent excess of alkylating agent for each hydroxyl group in tri-O-tritylsucrose. Thus, for example, if 100 mmol of tri-O-tritylsucrose is used, 500 mmol of hydroxyl groups/100 mmol tri-O-tritylsucrose react and therefore 2,500 mmol of alkylating agent is used.

The alkylating agent is added over a period of time at a variety of temperatures, which depend upon the alkylating agent used. For instance, if methyl iodide is used, the reaction should be cooled to 0° C. and should not rise above 10° C. during the reaction. The addition of said alkylating agent should be very slow to preclude the internal temperature of the reaction from rising to the boiling point since the alkylating agent may evaporate. The reaction is then stirred at room temperature for a period of between 2 to 24 hours. At this point, the mixture can be concentrated to one-fifth the volume at a temperature of about 60° C. under 0.1 mm Hg, if desired. Then the solution or concentrated solution is treated with a 10% solution of sodium hydroxide and stirred for an additional time period. After the addition of the sodium hydroxide, the resulting mixture is then diluted with water and an extracting agent such as methylene chloride or ethyl acetate. The extraction with the solvents is usually repeated at least twice, and the organic extracts are combined and further washed with water and brine. The washed organic extracts are then further dried over anhydrous magnesium sulfate, filtered, and concentrated in vacuo to provide a residue.

The residue is then placed over a silica gel column and the final product is eluted therefrom with a 1:1 hexane:methylene chloride solution of approximately 2 liters; followed by methylene chloride and 5% ethyl acetate in methylene chloride. The flow rate of the column varied between 100 ml/min to 200 ml/min.

The yield of 1',6,6'-tri-O-trityl-2,3,3',4,4'-penta-O-methylsucrose obtained by the above process is between 89% to 97%.

The 1',6,6'-tri-O-trityl-2,3,3',4,4'-penta-O-methylsucrose obtained is converted to 2,3,3',4,4'-penta-O-methylsucrose by unmasking the tri-O-trityl protecting groups to regenerate the hydroxyl groups at positions 140, 6 and 6'. The trityl groups are removed by reduction without adversely effecting the glycosidic linkage. This reductive cleavage is performed by using alkali metals in the presence of liquid ammonia in a suitable aprotic solvent such as tetrahydrofuran (THF). Alternatively the triphenylmethyl protecting groups may be removed by treatment of the trityl-O-pentamethyl adduct of sucrose with acetic acid. Here the yields are low, possibly due to cleavage of sucrose to produce O-methylated glucose and fructose derivatives.

Any alkali metal can be used in the present procedure such as lithium, sodium and the like. Two alkali metals may also be used such as lithium and sodium. It is preferable, however, to use lithium in this reduction procedure, because it is relatively inexpensive, is less reactive than other group (I) metals in air, is safe to handle in air and is less pyrophoric than any other group (I) metals in the presence of moisture.

The tritylated penta-O-methylsucrose is diluted in tetrahydrofuran (THF) and liquid ammonia. It is preferable to use approximately 1 liter of tetrahydrofuran for every 100 grams of tri-O-trityl-penta-O-methylsucrose; however, variations from this amount do not affect the yield of the final product. For example, 45 to 50 grams of tri-O-trityl-2,3,3',4,4'-penta-O-methylsucrose can be dissolved in 1.0 liter of tetrahydrofuran (THF), or 288 grams of tri-O-trityl-2,3,3',4,4'-penta-methylsucrose can be dissolved in 2.5 liters of THF. If 288 grams (253 mmol) of 1',6,6'-tri-O-trityl-2,3,3',4,4'-penta-O-methylsucrose is dissolved in 2.5 liters of dry tetrahydrofuran, then the mixture is cooled to −70° C. Into this solution is distilled approximately 2.5 liters of liquid ammonia, and the mixture is treated with small pieces of lithium (12 grams, 1,714 mmol, 6.7 equivalent). It is preferable to use 2 to 5 equivalent excess of lithium for each millimole of triphenylmethyl group present in the molecule. It is more preferable to use a minimum of 2 equivalent excess alkali metal per mole of the trityl moiety. The addition of the alkali metal generally takes place over a time period of 30 to 60 minutes depending upon the quantities involved. In this instance, the addition time is about 60 minutes. The color of the reaction mixture after addition of the alkali metal is deep red. The reaction mixture is allowed to stir for about three hours at a temperature between −65° C. to −78° C., more preferably at −70° C. The excess alkali metal is then decomposed by the addition of ethanol or isopropanol. However, it is preferable to use ethanol, since it can be easily removed in vacuo. Approximately 0.1 ml of ethanol is added per millimole of alkali metal used. Small pieces of solid carbon dioxide are also added after destroying the lithium metal to aid in the evaporation of ammonia as the solution is allowed to attain room temperature.

The resulting mixture is then filtered, the inorganic retentate is washed thoroughly with acetone, and the effluent is concentrated to a thick yellow oil. Flash column chromatography of the concentrated oil on a column of silica gel using 50% ethyl acetate in methylene chloride separates the triphenylmethane and other nonpolar components of the reaction mixture. 2,3,3',4,4'-Penta-O-methylsucrose is then eluted from the column with 10% ethanol in methylene chloride. The yield of the 2,3,3',4,4'-penta-O-methylsucrose from this isolation procedure is 95% to 97%.

Approximately between 2.06 grams (5 mmol) to 14.27 grams (34.62 mmol) of 2,3,3',4,4'-penta-O-methylsucrose in about 60 to 200 ml of a suitable solvent such as acetonitrile, dimethyl acetamide, pyridine and mixtures thereof; more preferably 6.2 grams (15.04 mmol) of 2,3,3',4,4'-penta-O-methylsucrose in about 150 ml of pyridine is then added to any trisubstituted phosphorus compound such as triphenylphosphine, triethylphosphine and the like. It is preferable to use triphenylphosphine followed by addition of a carbon tetrahalide of choice. It is most preferable to use carbon tetrachloride to form the dichloro derivative. The amount of triphenylphosphine used may vary depending on the amount of 2,3,3',4,4'-penta-O-methylsucrose used. For instance, between 7.8 grams (30 mmol) to 32.?5 grams (124.6 mmol) of triphenylphosphine, preferably 14.16 grams (54 mmol) can be used. It is most preferable to use 3.6 equivalents of triphenylphosphine.

After the addition of triphenylphosphine any tetrahalomethane may be used. Examples of the tetrahalomethanes that can be used in the present invention include carbon tetrachloride, carbon tetraiodide, carbon tetrabromide and the like.

The amount of the tetrahalomethane that is used may vary depending upon the amount of 2,3,3',4,4'-penta-O-methylsucrose and triphenylphosphine used. The amount of tetrahalomethane may vary between 4.615 grams (30 mmol) to 19.193 grams (124.63 mmol). It is preferable to use 8.312 grams (54 mmol) of tetrahalomethane in the present invention. The additic: of the tetrahalomethane usually takes place at ambient room temperature that may vary between 20° C. to 28° C. It is preferable to add the tetrahalomethane at a temperature of 25° C.

After addition of the tetrahalomethane, the contents are then further stirred vigorously and allowed to attain a temperature of about 60° C. over about 40 minutes. After the reaction has reached the temperature of 60° C., the reaction is monitored to ensure that all of the starting material is consumed by aliquoting a 10 μl sample from the reaction every 15 minutes and running a TLC plate in ethyl acetate (silica gel 60, E Merck). Generally all of the starting material is consumed between 60 to 75 minutes.

Methanol, ethanol or propanol is then added to the reaction mixture to stop the reaction. It is preferable to use methanol since it can be conveniently removed in vacuo. The amount of methanol added to the reaction is not critical and may range from 50 to 300 ml. The amount used may vary depending on the amount of penta-O-sucrose used in the reaction. For instance, it is preferable to use about 100 ml for 6 grams of the penta-O-methylsucrose used in the reaction or 300 ml for 14 grams of the penta-O-methylsucrose. The contents are then cooled to room temperature and concentrated to a paste in vacuo.

The residue is then dissolved in ethyl acetate and washed three times with 10% aqueous hydrogen peroxide. The organic layer is separated and placed in a refrigerator for a few hours or overnight to allow the triphenylphosphine oxide to precipitate. The phosphine oxide is removed by filtration and the effluent adsorbed onto silica gel (100 grams) and further concentrated to a dry, free-flowing powder. The silica gel-coated mixture is then carefully poured onto a column of silica gel and eluted with 30% ethyl acetate in hexanes to provide a 6,6'-dihalo-6,6'-dideoxy-2,3,3',4,4'-penta-O-methylsucrose as an oil.

6,6'-Dihalo-6,6'-dideoxy-2,3,3',4,4'-penta-O-methylsucrose is then diluted in methylene chloride and treated with boron trifluoride etherate, followed by addition of excess diazomethane in methylene chloride to methylate the 1' oxygen moiety.

A solution of the dihalide, generally between 646 milligrams (1.44 mmol) to 28.55 grams (63.56 mmol) is used, more preferably 4.28 grams (9.53 mmol). The dihalide solution is cooled to a temperature of about $-10°$ C. Between 10 $\mu$l to 100 $\mu$l of boron trifluoride etherate is added to this solution. It is preferable to add between 50 $\mu$l to 70 $\mu$l of boron trifluoride etherate. The boron trifluoride etherate is added dropwise to the cooled dihalopenta-O-methylsucrose in methylene chloride solution.

After the boron trifluoride etherate is added an excess amount of diazomethane in methylene chloride is added very slowly as a stream to the solution at $-10°$ C. Subsequently, it is critical to add the boron trifluoride etherate very slowly to the solution and the solution must be cooled to $-10°$ C. to prevent an explosion. This reaction is spontaneous and thus the solution is then filtered immediately after the addition of the boron trifluoride etherate and is washed serially with sodium bicarbonate, water and brine. The organic layer is then separated and dried over anhydrous magnesium sulfate prior to concentrating this layer in vacuo. 6,6'-Dihalo-6,6'-dideoxy-1',2,3,3',4,4'-hexa-O-methylsucrose is the product which is obtained as an oil. Alternatively, the solution following the treatment with diazomethane can be briefly purged with argon, poured over a short bed of silica gel in a sintered glass funnel, filtered, and the effluent collected. The silica gel bed is washed with ethyl acetate in hexanes (1:1) to recover all the product. The organic layers are concentrated in vacuo to provide the dihalo-dideoxy-hexa-O-methyl adduct as an oil.

The dihalo-hexa-O-methyl intermediate is converted to the diol monomer in two steps. Displacement of the dihalides with cesium acetate, followed by hydrolysis of the acetates provides the final compound of structure (I). The dihalo-hexa-O-methyl sucrose derivative is added to a suspension of cesium acetate in dry dimethylformamide. The cesium acetate was prepared by method of Huffman, J. W. and Desai, R. W., *Synthetic Communications*, 13, pp. 553-557 (1983). To a solution of cesium carbonate 1.075 grams (3.3 mmol) in dry methanol (33 ml) is added freshly distilled acetic acid (0.566 ml, 594 mg, 9.9 mmol; 3.0 equivalents/mol cesium carbonate). The solution is stirred for one hour at room temperature and the methanol and acetic acid removed in vacuo to produce a white powder. The power was resuspended in 5 ml toluene and the toluene distilled in vacuo at 40° C., 0.1 mm Hg to remove all traces of acetic acid. The cesium acetate obtained by aforementioned method is diluted in DMF. Generally, between 2 ml to 5 ml DMF is used, preferably about 5 ml per gram 6,6'-dihalo-(OMe)$_6$-sucrose. The amount of cesium acetate may vary depending upon the amount of dihalide used. For instance, if 1.0 gram of the dihalide is used, then 2.48 grams of cesium acetate is used. Generally and most preferably 3 equivalents of cesium acetate is used per millimole of halide. For example, if 1 gram dichloride 2.48 grams cesium acetate is used.

The reaction mixture is then stirred at a temperature between 100° C. to 130° C., preferably 130° C. for 48 hours, prior to cooling the mixture to room temperature. The cooled solution is then diluted with water and extracted with methylene chloride. The combined organic extracts are then washed with water and then brine and finally concentrated in vacuo. The concentrated sample is then further purified on a silica gel column and eluted with 50% ethyl acetate in hexanes. The final product of 6,6'-diacetoxy-1',2,3,3',4,4'-hexa-O-methylsucrose is eluted as an oil.

The diacetate compound is then diluted in methanol and a 2M solution of sodium methoxide in methanol is added dropwise over a period of 15 minutes. Generally, between 1.08 grams to 1.18 grams of the diacetate is diluted in methanol. The amount of methanol that is added is not critical but generally 20 ml to 40 ml is used. Then the diacetate solution is treated with an excess of 2M sodium methoxide in methanol at 0° C. Typically between 10 ml to 20 ml of the 2M sodium methoxide solution is added. The pale yellow solution is then allowed to attain room temperature and stirred at room temperature for about 2 hours and concentrated in vacuo. The concentrated solution is diluted with water and acidified to a pH of 7.0 by dropwise addition of 1M hydrochloric acid. The acidified mixture is then concentrated to a solid residue reconstituted in 1 ml ethyl acetate in methylene chloride (95:5) and applied directly on a silica gel column. 1',2,3,3',4,4'-hexa-O-methylsucrose is eluted from the silica gel with 95% ethyl acetate:5% methylene chloride.

1',2,3,3',4,4'-Hexa-O-methylsucrose may be used to make water absorbent polyesters and polyethers and is easily oxidized to a dicarboxylic acid which may also be used to make other novel polyesters or polyamides. Polyamines can also be synthesized from hexa-O-methylsucrose by oxidation of the 6,6'-hydroxyl groups to the corresponding 6,6'-dialdehydes followed by reductive coupling with an appropriated alkyl or aryl diamine to provide the desired polyamine. Examples of the alkyl diamines that can be used include ethylene diamine, 1,3-diaminopropane, 1,4-diaminobutane, 1,5-diaminopentane, and the like. Examples of aryl diamines that can be used include p-methyleneaminobenzylamine, 2,6-diaminonaphthalene, and the like. The temperature of the reaction ranges from 100° C. to 120° C.

In the synthesis of polyethers, the 6,6'-dihydroxy groups on the hexa-O-methylsucrose, may be deprotonated by a suitable non-nucleophilic base, and treated with alkyl or benzylic dihalides to produce the desired polyethers. Examples of the suitable non-nucleophilic bases that can be used in the present invention include sodium hydride, lithium hydride, potassium hydride, and the like. Examples of the alkyl dihalide that can be used are 1,2-dichloroethane, 1,3-dichloropropane, 1,4-dichlorobutane, and the like. Examples of the benzylic dihalide that can be used include p-chloromethylene benzylchloride, 2,6-dichloromethylenonaphthalene, and the like. The temperature of the reaction may vary between 60° C. to 120° C. These reactions are analogous to the classical Williamson ether synthesis.

Yet, another example of the use of the diol in the present invention is to use an electrophile which is capable of reacting with the diol in an aromatic nucleophilic substitution reaction. Certain aromatic chlorides and nitro compounds which are activated by $SO_2$ groups by electron-withdrawing imides in the para position may be displaced to produce polyether sulfones or polyether imides. Polyether ketones may also be prepared using hexa-O-methyl sucrose by reactions involving the displacement of aromatic fluorides which are activated in the para position by ketones.

These diols can also lead to the synthesis of various polyesters upon treatment with dicarboxylic acids, their acid chlorides and anhydrides.

Oxidation of 1',2,3,3',4,4'-hexa-O-methylsucrose with basic or neutral reagents can lead to the formation of a diacid in which the 6 and 6' positions are carboxylic acid moieties. The diacid may then be used to make polyesters or polyamides by methods known in the art or may be converted to the corresponding acid chloride by treatment with thionyl chloride.

The diacid, the diacid chloride or the dialdehyde may be reacted with diamines under high dilution conditions to produce many different ionophores. Similarly the diacid chloride may be treated with a variety of diols under high dilution conditions to produce macrocyclic bis lactones that may also act as ionophores.

Polyamines can also be prepared by oxidizing the diol in 1',2,3,3',4,4'-hexa-O-methylsucrose to the 6,6'-dialdehyde. Reductive coupling of the dialdehyde with appropriate diamines would then produce the desired polyamines.

In order to further illustrate the present invention and the advantages thereof, the following specific examples are given, it being understood that same are intended only as illustrative and in nowise limitative.

EXAMPLE 1

A. Synthesis of 1',6,6'-tri-O-tritylsucrose

The procedure of Hough, Mufti, and Khan, *Carbohydrate Res.*, Vol. 21, pp. 144–147 (1972), is modified as shown below. To a solution of 15 g of sucrose (43.82 mmol) in 225 ml of pyridine, a solution of 54.95 g of trityl chloride (197.1 mmol, 4.5 equiv.) in 50 ml of pyridine is added dropwise over a period of 30 minutes. The reaction mixture is then stirred at room temperature for 4 days. After 4 days, the solution is concentrated to a brown syrup, which is dissolved in methylene chloride. This solution is further washed successively with 1M hydrochloric acid, saturated sodium bicarbonate solution, water, and brine and then dried over anhydrous sodium sulfate. The methylene chloride solution it then concentrated in vacuo and the residue applied on a column of silica gel packed in methylene chloride:acetone (4:1) and eluted with that solvent. The 1',6,6'-tri-O-tritylsucrose is obtained (28.59 g) in 58.8% yield as an off-white solid with a melting point of 127° to 130° C.

B. Synthesis of 1',6,6'-tri-O-tritylsucrose

On scales larger than 40 mmol, the following procedure can be used. However, the yields established in the method shown are reproducible on scales ranging from 1 mmol to 210 mmol.

In a dry 5-L four-neck flask is dissolved 70 grams of sucrose (204.5 mmol) in 1 liter dry dimethylformamide (DMF) and dry triethylamine (200 ml, 145 grams, 1,423 mmol). The solution is allowed to attain a temperature of 25° to 30° C. and treated with a solution of trityl chloride (260 grams, 935.2 mmol, 4.5 equiv.) in dimethylformamide (600 ml), added dropwise over 1 hour. After the addition is complete, the reaction mixture is heated to a temperature of 50° C. and allowed to stir for 48 hours at that temperature. After 2 days, the reaction mixture is filtered through a short pad of silica gel to remove the precipitated triethylammonium hydrochloride and the residue is washed with methylene chloride:acetone (4:1). The effluent is then concentrated to a residue, which is reconstituted in methylene chloride and washed successively with 1N hydrochloric acid, saturated sodium bicarbonate solution, water, and brine and then dried over anhydrous sodium sulfate. The dry organic extract is then filtered and concentrated in vacuo to provide a yellow foamy solid. This material is then applied on a silica gel column (230 to 400 mesh, 10 cm×50 cm) packed with methylene chloride and successively eluted with methylene chloride, then 10% acetone in methylene chloride, followed by elution with 20% acetone in methylene chloride. The desired tri-O-tritylsucrose elutes with 20% acetone in methylene chloride and has an $R_f$ of 0.21 in the same solvent. The amount of 1',6,6'-tri-O-tritylsucrose obtained by this method of synthesis and isolation is typically between 146 to 150 grams or 67% to 68.8%. On scales between 1 mmol and 50 mmol (314 mg to 15.7 grams) yields average about 76%.

Figure 2:
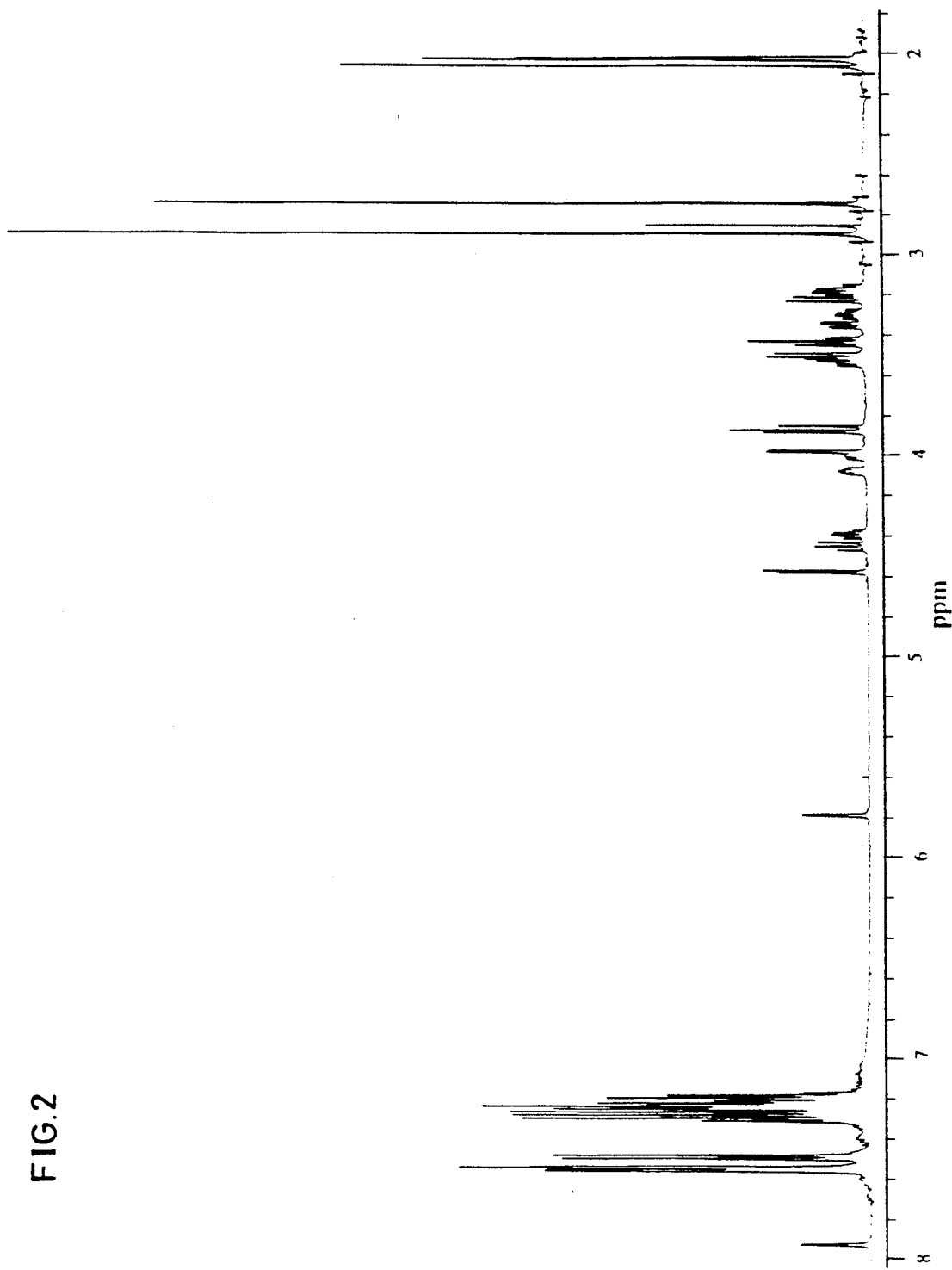
FIG. 2 is an $^1$H NMR spectrum of 1',6,6'-tri-O-tritylsucrose synthesized by the process of the present invention.
Figure 3:
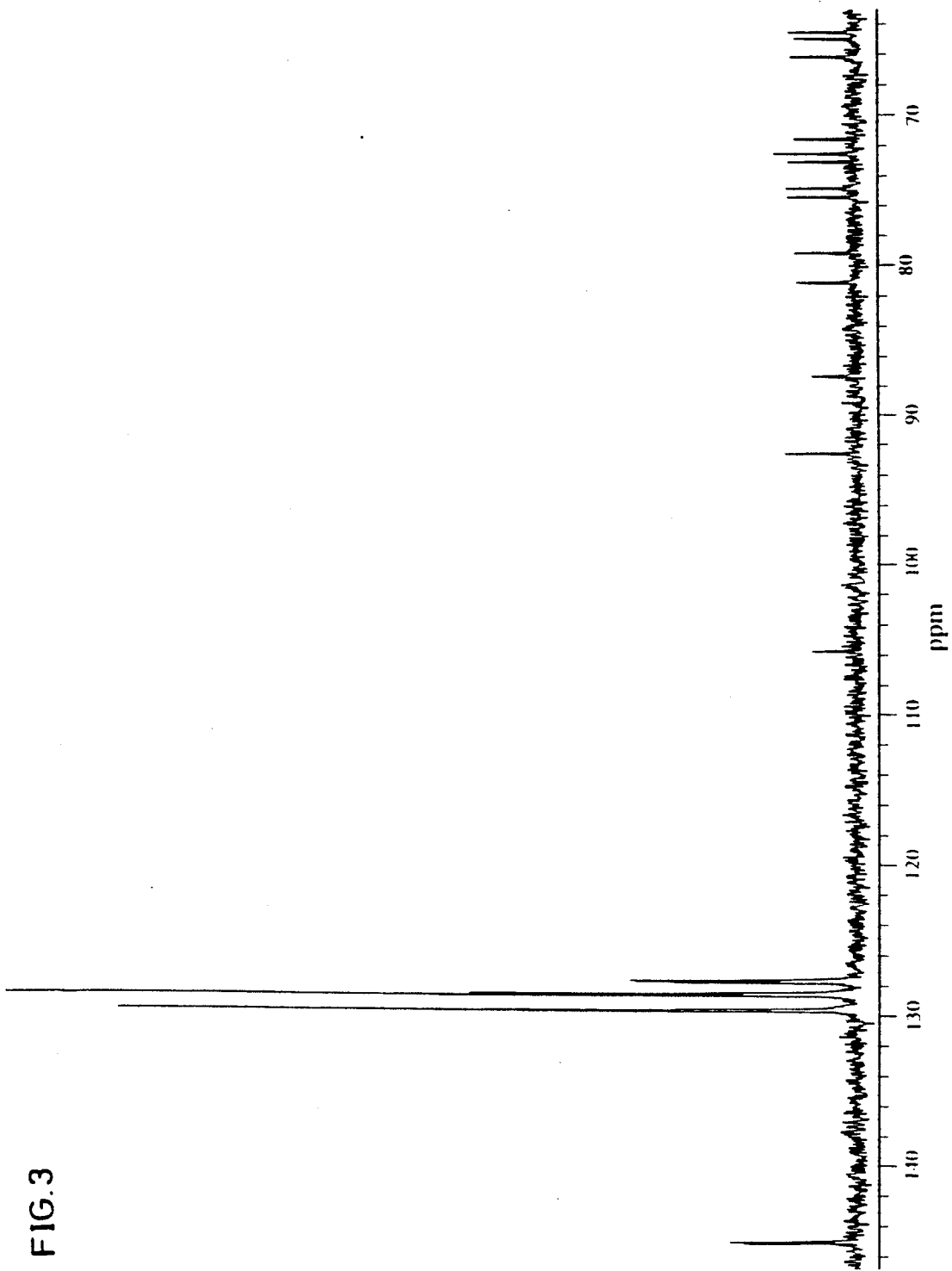
FIG. 3 is a $^{13}$C NMR spectrum of 1',6,6'-tri-O-tritylsucrose synthesized by the process of the present invention.

FIGS. 2 and 3 illustrate the respective NMR spectra of 1',6,6'-tri-O-tritylsucrose.

C. Synthesis of 1',6,6'-tri-O-trityl-2,3,3',4,4'-penta'-O-methylsucrose

Figure 4:
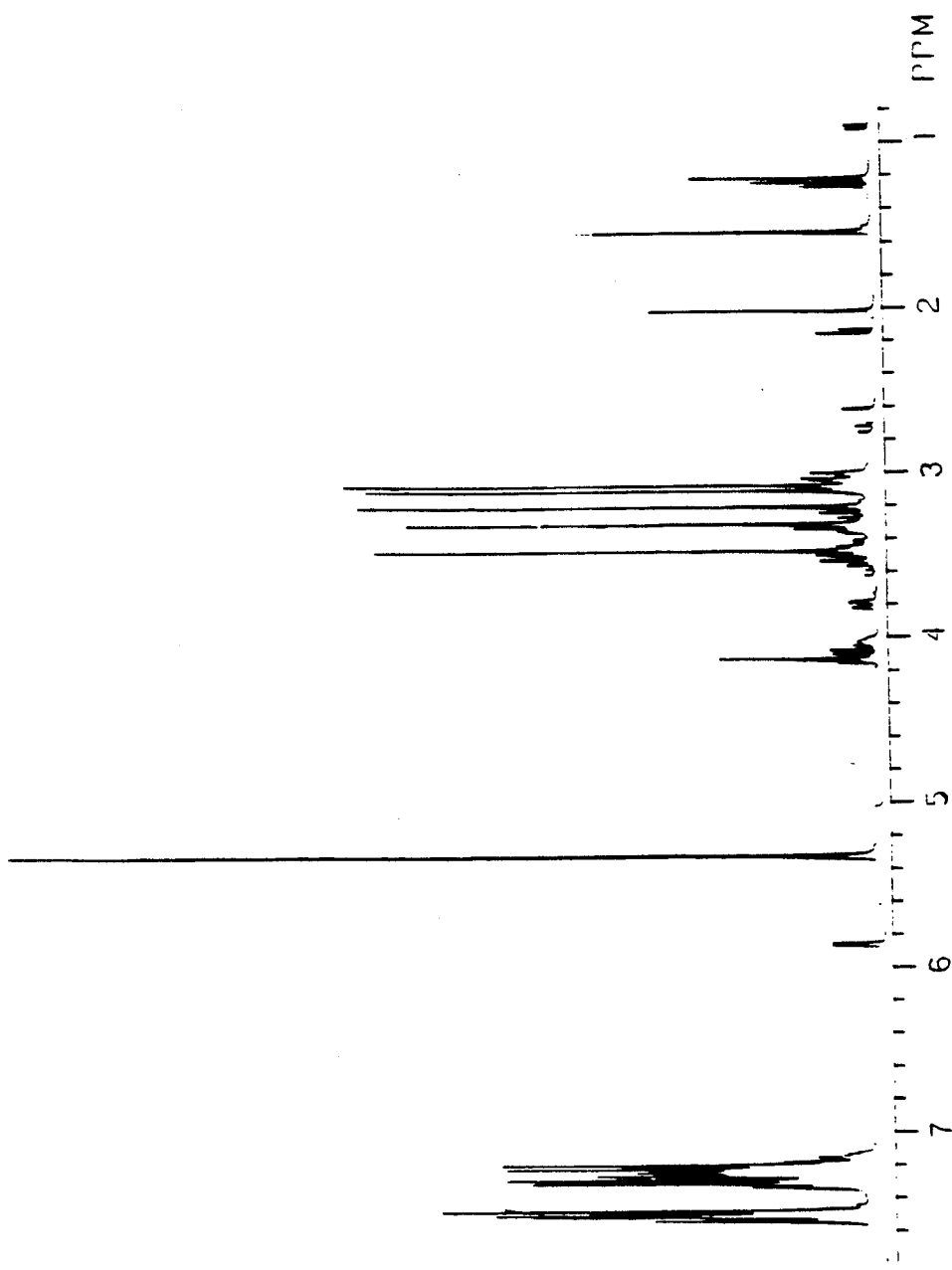
FIG. 4 is an $^1$H NMR spectrum of 1',6,6'-tri-O-trityl-2,3,3',4,4'-penta-O-methylsucrose synthesized by the process of the present invention.
Figure 5:
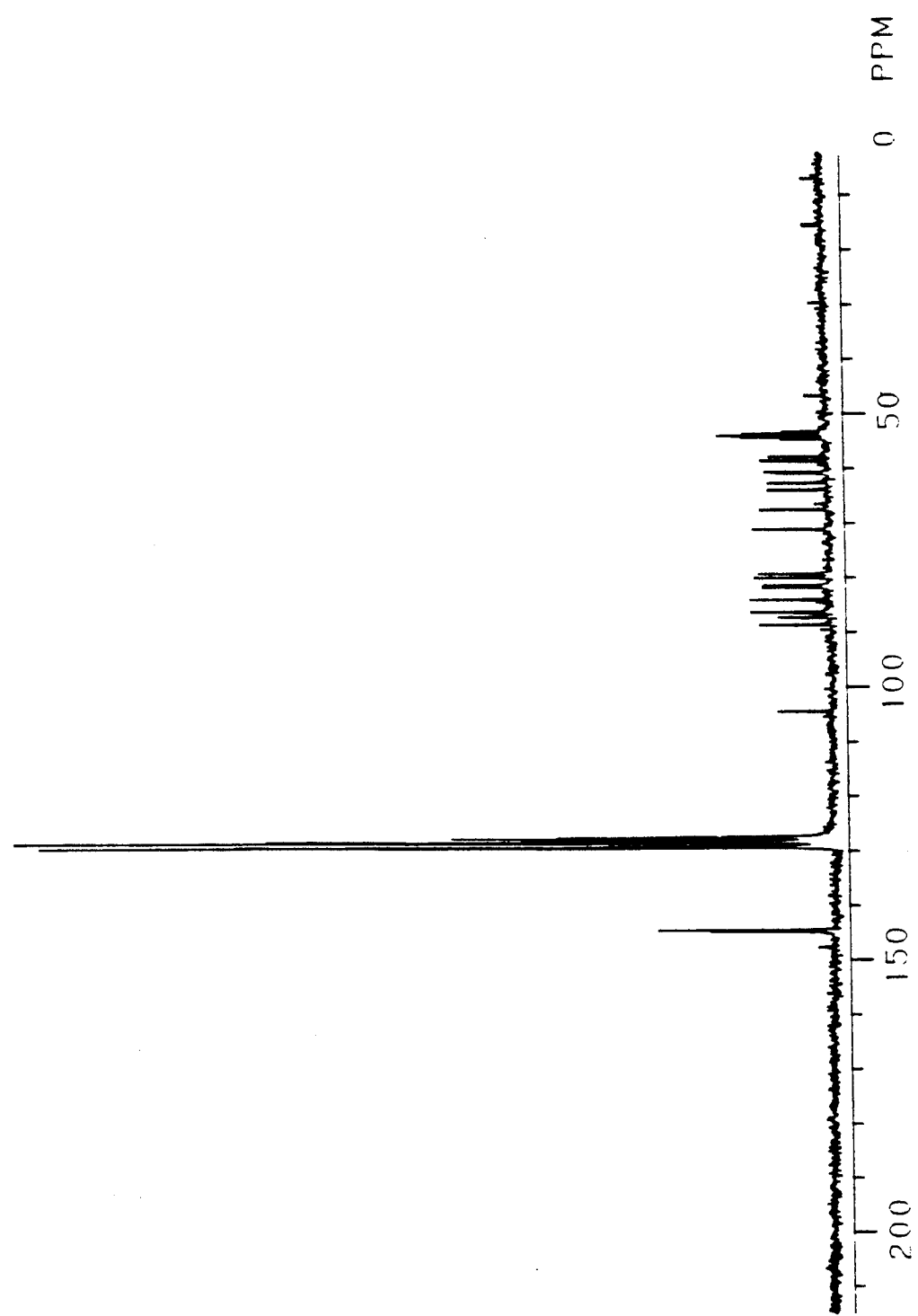
FIG. 5 is a $^{13}$C NMR spectrum of 1',6,6'-tri-O-trityl-2,3,3',4,4'-penta-O-methylsucrose synthesized by the process of the present invention.

On scales larger than 10 mmol the following procedure is used. To a dry 5-L four-neck flask is added sodium hydride (60% in oil, 150 grams, 1250 mmol), washed free of oil with pentane and suspended in DMSO (800 ml). The suspension is heated to 50° C., mechanically stirred, and treated with a solution of 1,6,6'-tri-O-tritylsucrose (50 grams, 46.76 mmol, dissolved in DMSO 200 ml, and added dropwise over 2 hours). The temperature of the reaction is monitored internally and maintained between 50° C. and 55° C. during the course of addition and 90 minutes thereafter. After hydrogen evolution has ceased completely, the burgundy-red solution is cooled to 25° C. and treated with dimethyl sulfate (147.5 grams, 1175 mmol, 111 ml, added dropwise over 90 minutes). The reaction is stirred at room temperature for 24 hours, treated with aqueous sodium hydroxide (10% solution, 500 ml), and stirred for an additional 3 hours. The mixture is then diluted with water (500 ml) and methylene chloride (500 ml) and the phases separated. The aqueous layer is re-extracted with methylene chloride (4×300 ml), then the organic extracts are combined, washed with water and brine, dried over anhydrous magnesium sulfate, filtered, and concentrated in vacuo. The glassy residue is flash-chromatographed over a column of silica gel (10 cm×15 cm) and eluted with hexanes:methylene chloride (1:1, 2L), then methylene chloride (2L) followed by 5% ethyl acetate in methylene chloride (2L), at a flow rate of about 200 ml/min. The isolated product (mp 103°–108° C.) weighed 47.1 grams (41.35 mmol) and a 89% yield is obtained. $R_f$ of the tritylated methylsucrose is 0.15 in methylene chloride and $[\alpha]_D^{27}=47.68°$ in methylene chloride. FIGS. 4 and 5 illustrate the respective NMR spectra for this product. The NMR data provided: $^1$H NMR (500.11 MHz, acetone-D$_6$) δ 3.04 (H-2, dd, J=3.5, 9.5 Hz), 3.06 (H-1′a, d, J=10 Hz), 3.07 (H-6a, dd, J=3, 10 Hz), 3.14 (OMe-3′, s), 3.16 (OMe-4′, s), 3.19 (OMe-2, s), 3.21 (H-3, t, J=9.5 Hz), 3.31 (OMe-4, s), 3.36 (H-1′b, d, J=10 Hz), 3.41 (OMe-3, s), 3.41 (H-6b, J=2, 10 Hz), 3.51 (H-6′a, m), 3.53 (H-4, dd, J=9.5, 10 Hz), 3.55 (H-6′b, m), 3.88 (H-5, ddd, J=2, 3, 10 Hz), 4.17 (H-3, d, J=8.5 Hz), 4.29 (H-4′, t, J=8.5 H) 4.41 (H-5′, m), 5.98 (H-1, d, J=3.5 Hz), 7.34 (30H arom), 7.52 (15H arom). $^{13}$C NMR (125.76 MHz, acetone-D$_6$) δ 57.73 (OMe-3′), 58.36 (OMe-4′), 58.68 (OMe-2, 60.46 (OMe-4), 60.60 (OMe-3), 62.97 (CH$_2$-6′), 63.89 (CH$_2$-6), 67.86 (CH$_2$-1′), 71.41 (CH-5), 79.52 (CH-5′), 80.17 (CH-4), 81.50 (CH-4′), 82.35 (CH-2), 84.52 (CH-3), 86.74 (1′-C-trityl methine), 86.93 (CH-3′), 87.51 (6-C-trityl methine), 87.68 (6′-C-trityl methine), 88.92 (CH-1), 104.66 (CH-2′), 127.22 (CH), 127.43 (2CH), 128.07 (2CH), 128.23 (3CH), 128.27 (CH), 129.03 (2CH), 129.14 (4CH), 144.05(C); 144.32 (2C); FAB mass for C$_{74}$H$_{74}$O$_{11}$ calculated 1138.33; found M$^+$ +1=1139, M$^+$- H+K$^+$=1177, M$^+$+K$^+$=1178. Anal. Calc. for C$_{74}$H$_{74}$O$_{11}$:C, 78.0; H, 6.5; O, 15.5. Found: C, 77.5; H, 6.5.

After scale-up of this reaction employing 150 g tri-O-tritylsucrose (140 mmol), 150 g of sodium hydride (60% in oil, 3,900 mmol); 1,600 ml of dimethylsulfoxide; and 330 ml of dimethylsulfate (441 g, 3,500 mmol) was performed under exactly the same conditions discussed above. After chromatography on a column of silica gel (230 to 400 mesh, 10 cm×50 cm) and elution with three times the quantities of solvents discussed above, 145.15 g of tri-O-trityl-penta-O-methylsucrose was obtained in 91% yield.

D. Synthesis of 2,3,3′,4,4′-penta-O-methylsucrose

To a 40 mmol solution of 1′,6,6′-tri-O-trityl-2,3,3′,4,4′-penta-O-methylsucrose (45.6 grams) in 1 liter of dry tetrahydrofuran and 2 liters of liquid ammonia at −70° C. is added 4 grams of small pieces of lithium wire. The lithium wire is added over a period of over 50 minutes and a deep-red solution is obtained. This solution is further stirred for 3 hours at −70° C. The excess lithium is decomposed by adding 60 ml of ethanol. Small pieces of solid carbon dioxide are also added to evaporate the ammonia as the solution approaches room temperature. The resulting mixture is then filtered, and the inorganic retentate is washed thoroughly five times with 300 ml of acetone. The effluent is then concentrated to a thick yellow oil.

The product is then purified by flash column chromatography according to the guidelines of Still, Kahn and Mitra, *J. Org. Chem.*, Vol. 43 (1978), pp. 2923–2925, on 230–400 mesh silica gel.

The oil is then placed on a silica gel column (10 cm×15 cm) and is washed with a solution containing 50% ethyl acetate in methylene chloride at a flow rate of 200 ml/min. This wash separates out the triphenylmethane and other nonpolar components of the reaction mixture.

Figure 6:
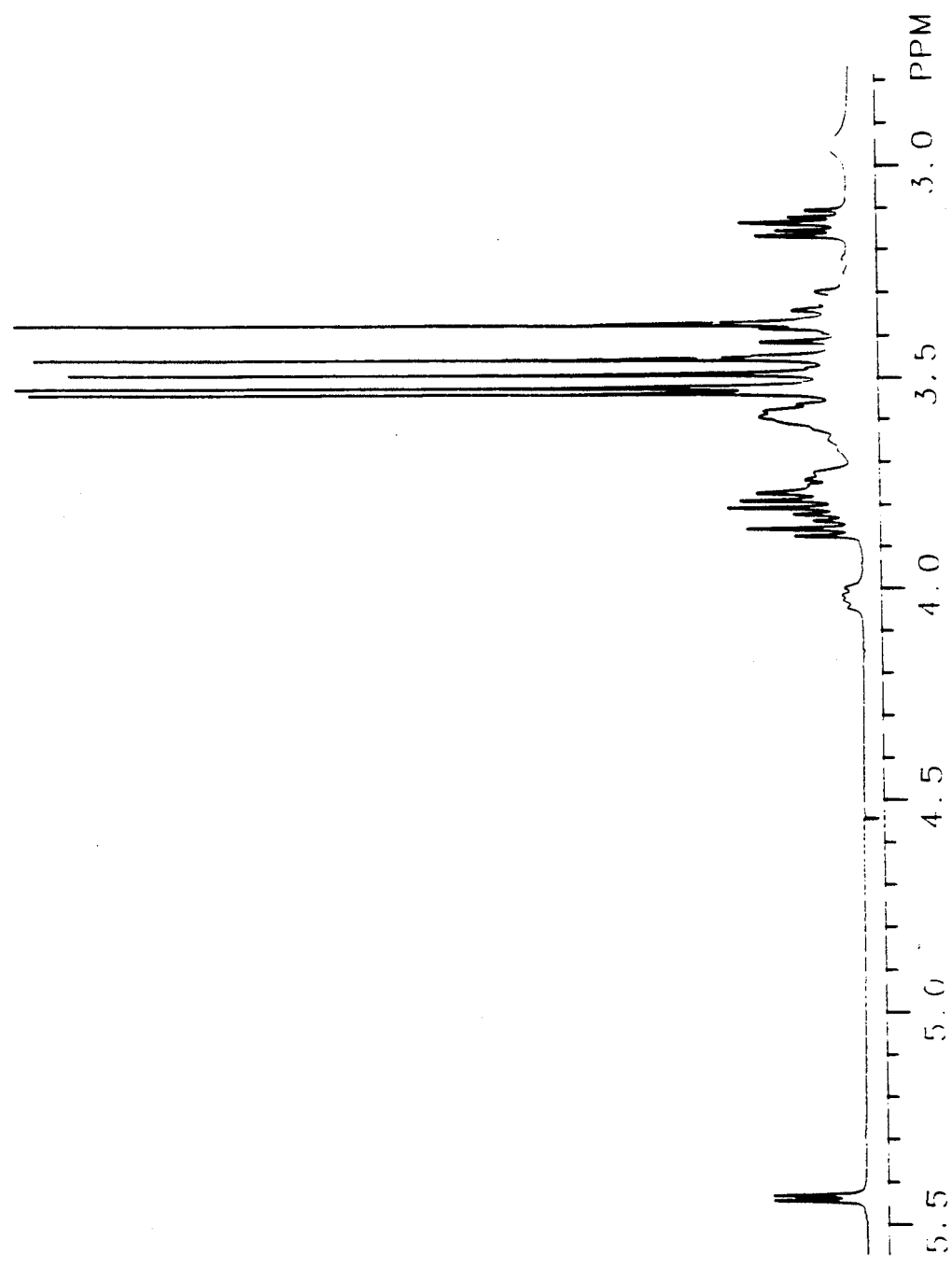
FIG. 6 is an $^1$H NMR spectrum of 2,3,3',4,4'-penta-O-methylsucrose synthesized by the process of the present invention.
Figure 7:
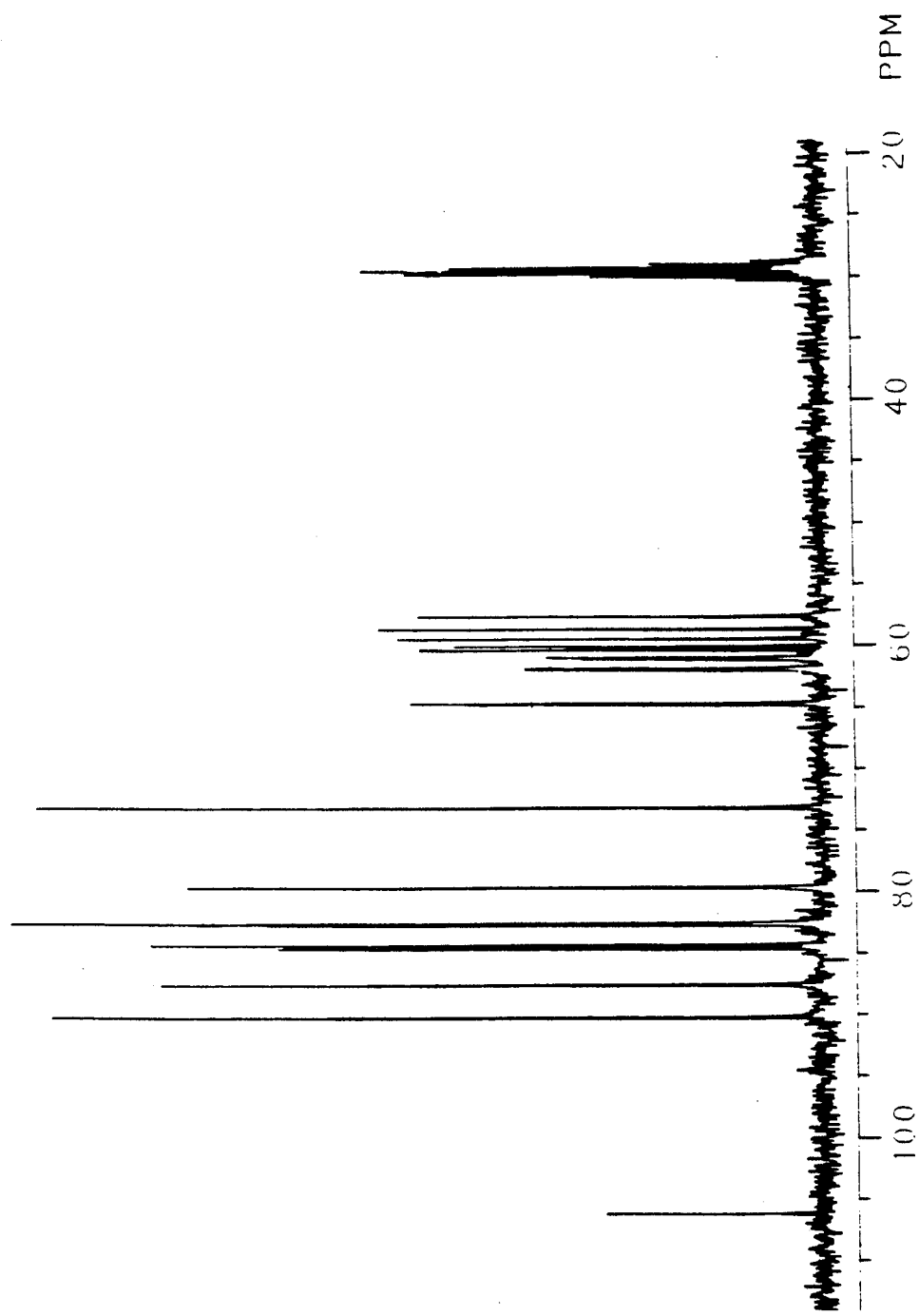
FIG. 7 is a $^{13}$C NMR spectrum of 2,3,3',4,4'-penta-O-methylsucrose synthesized by the process of the present invention.

2,3,3′,4,4′-Penta-O-methylsucrose is eluted from the column with a 10% ethanol in methylene chloride solution. 16.11 Grams, 39.10 mmol of 2,3,3′,4,4′-penta-O-methylsucrose is obtained, and the yield of this product is 97%. R$_f$ in 5% ethanol in methylene chloride is 0.31 and $[\alpha]_D^{27}$=50.60° in acetone. $^1$H NMR (500.11 MHz, acetone D$_6$) δ 3.15 (H-4, t, J$_{3',4'}$=5.1 Hz, J$_{4,5}$=9.0 Hz), 3.15 (H-2, dd, J$_{1,2}$=3.7 Hz, J$_{2,3}$=9.8 Hz), 3.33 (H-1′a, d, J$_{1'a,1'b}$=−12.5 HZ), 3.38 (OMe-4′, s), 3.40 (H-3, t, J$_{3,4}$=9.8 Hz), 3.46 (OMe-3′, s), 3.50 (OMe-2, s), 3.53 (OMe-4, s), 3.55 (OMe-3, s), 3.55 (H-1′b,d), 3.59 (H-6′a, m, J$_{6'a,6'b}$=12.0 Hz), 3.60 (H-6a, dd, J$_{5,6a}$=5 Hz, J$_{6a,6b}$=−10.6 Hz), 3.61 (H-6′b, m J$_{6'a,6'b}$=−12.0 Hz), 3.75 (H-6b, dd, J$_{5,6b}$=2.1 Hz, J$_{6a,6b}$=10.6 Hz), 3.78 (H-5, m, J$_{5,6a}$=5 Hz, J$_{5,6b}$=2.1 Hz), 3.80 (H-4′, t, J$_{3',4'}$=5.1 Hz, J$_{4',5'}$=5.8 Hz), 3.84 (H-5′, m, J$_{5',6'a}$=4.2 Hz, J$_{5',6'b}$=6.3 Hz), 3.87 (H-3′, d, J$_{3',4'}$=5.1 Hz), 5.45 (H-1, d, J$_{1,2}$=3.7 Hz). $^{13}$C NMR (125.76 MHz, acetone D$_6$) δ 57.96 (OMe-4′), 58.98 (OMe-3′), 59.76 (OMe-2), 60.29 (CH$_2$-6), 60.39 (OMe-4), 60.67 (OMe-3), 61.79 (CH$_2$-6′), 64.63 (CH$_2$-1′), 73.12 (CH-5), 79.53 (CH-2), 82.48 (CH-4), 82.59 (CH-5′), 84.24 (CH-3), 84.52 (CH-4′), 87.48 (CH-3′), 90.17 (CH-1), 106.80 (C-2′). FDMS for C$_{17}$H$_{32}$O$_{11}$ calculated 412.43; found M+1=413. Anal. Calc. for C$_{17}$H$_{34}$O$_{11}$: C, 49.5; H, 7.5; O, 42.8 Found: C, 49.2; H, 7.8. FIGS. 6 and 7 illustrate the respective NMR spectra of 2,3,3′,4,4′-penta-O-methylsucrose.

E. Synthesis of 6,6′-dichloro-6,6′-dideoxy-1,2,3,3′,4,4′-hexa-O-methylsucrose To a solution containing 2,3,3′,4,4′-penta-O-methylsucrose (6.2 g. 15.04 mmol) in pyridine (150 ml) is added triphenylphosphine (14.16 g, 54 mmol, 3.6 equiv.) followed by carbon tetrachloride (8.31 g, 5.19 ml, 54 mmol) at 25°. The contents are stirred vigorously and allowed to attain a temperature of 60° over 40 min., then maintained at that temperature for an additional 30 min. To this mixture is added methanol (100 ml), then the contents are cooled to room temperature and concentrated to a paste in vacuo. The residue is redissolved in ethyl acetate and washed with 10% hydrogen peroxide (3×100 ml). The organic layer is then adsorbed onto silica gel (100 g) and further concentrated to a dry, free-flowing powder. The silica gel-coated mixture is carefully poured onto a column (5 cm×15 cm) and eluted with 30% ethyl acetate in hexanes to provide 6,6′-dichloro-6,6′-dideoxy-2,3,3′,4,4′-penta-O-methylsucrose 4 as an oil (6.2 g, 13.8 mmol, 91.7% yield). R$_f$ of 6,6′-dichloro-6,6′-dideoxy-2,3,3′,4,4′-penta-O-methylsucrose in 50% ethyl acetate in hexanes is 0.29, $[\alpha]_D^{26}$=40.13 in acetone. This compound is used immediately without further characterization.

A solution of 6,6′-dichloro-6,6′-dideoxy-2,3,3′,4,4′-penta-O-methylsucrose (6.2 g, 13.8 mmol) in methylene chloride (50 ml) at −10° is treated with boron trifluoride etherate (70 μl ), followed by addition of excess diazomethane in methylene chloride (approximately 0.7M, 100 ml, 70 mmol). After about 5 min., the cold solution is filtered and washed serially with saturated sodium bicarbonate, water, and brine. The organic layer is dried over anhydrous magnesium sulfate and concentrated in vacuo to provide the dichloro-hexa-O-methyl ether as an oil (6.33 g, 13.66 mmol, 99% yield). This compound needed no further purification. R$_f$ of 6,6′-dichloro-6,6′-dideoxy-2,3,3′,4,4′-hexa-O-methylsucrose in 50% ethyl acetate in hexanes is 0.48, $[\alpha]_D^{25}$=58.15°. $^1$H NMR (500.11 MHz, acetone-D$_6$) δ 3.07 (H-4, dd, J=9, 9.5 Hz), 3.08 (H-2, dd, J=3.5, 9.5 Hz), 3.36 (H-1′b, d, J=11 Hz), 3.38 (H-3, t, J=9.5 Hz), 3.38 (OMe-1′, s), 3.43 (OMe-2, s), 3.46 (OMe-4′, s), 3.47 (OMe-3′, s), 3.53 (OMe-4, s), 3.53 (OMe-3, s), 3.58 (H-1′a, d, J=11 Hz), 3.75-3.92 (6H, m), 4.01 (H-3′, d, J=7 Hz), 4.01 (H-5, ddd, J=2.5, 5, 9.5 Hz), 5.51 (H-1, d, J=3.5 Hz). $^{13}$C NMR (125.76 MHz, acetone D$_6$) δ 45.60 (CH$_2$-6), 46.25 (CH$_2$-6'), 58.20 (OMe-2), 58.31 (OMe-4'), 58.49 (OMe-3'), 59.08 (OMe-1'), 60.33 (OMe-3), 60.35 (OMe-4), 71.03 (CH-5), 73.99 (CH$_2$-1'), 80.56 (CH-4), 81.10 (CH-5), 82.21 (CH-2), 83.75 (CH-3), 85.75 (CH-4'), 85.98 (CH-3'), 89.96 (CH-1), 105.2 (C-2').

Figure 8:
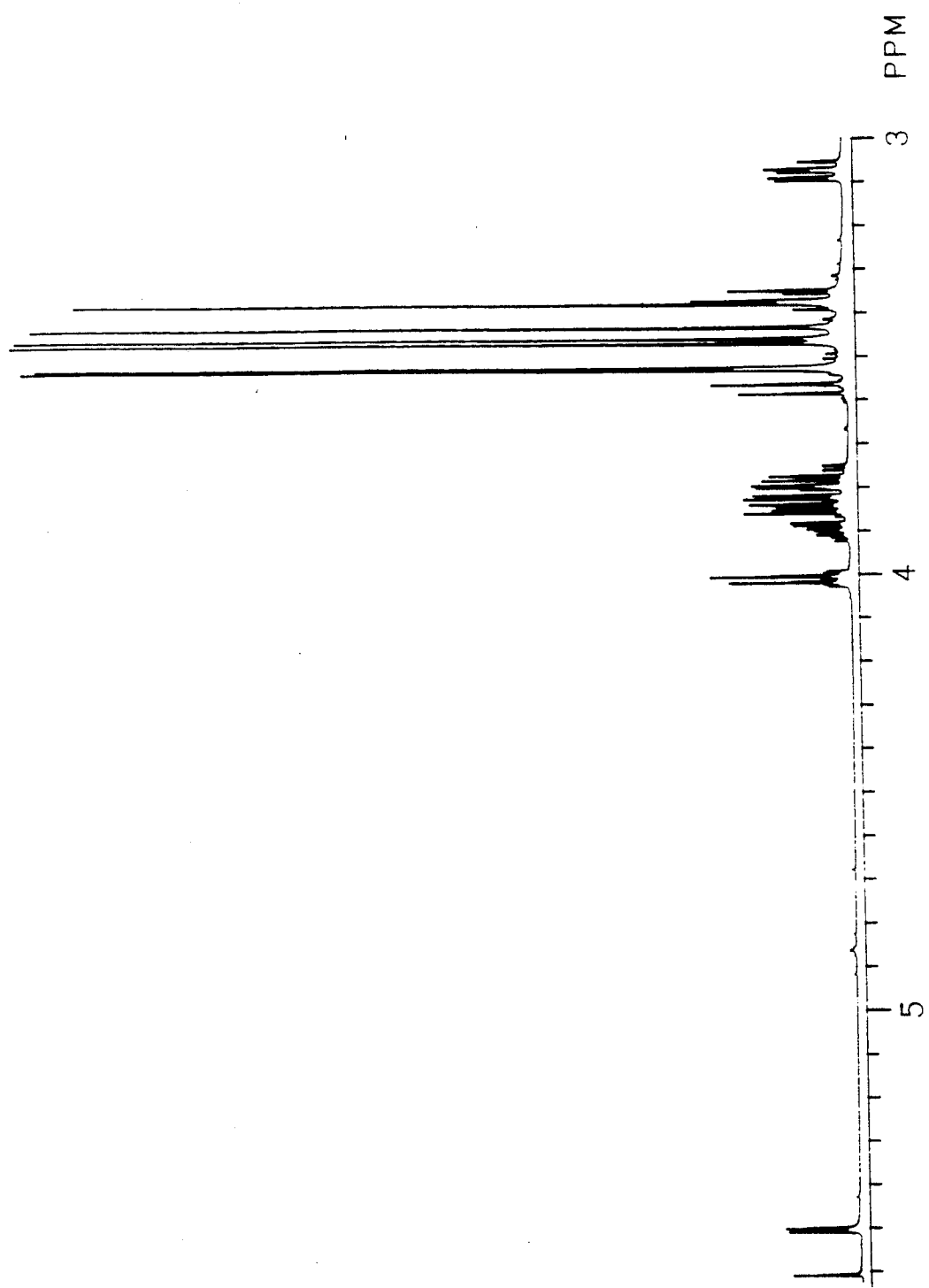
FIG. 8 is a $^1$H NMR spectrum of 6,6'-dichloro-6,6'-dideoxy-1',2,3,3',4,4'-hexa-O-methylsucrose synthesized by the process of the present invention.
Figure 9:
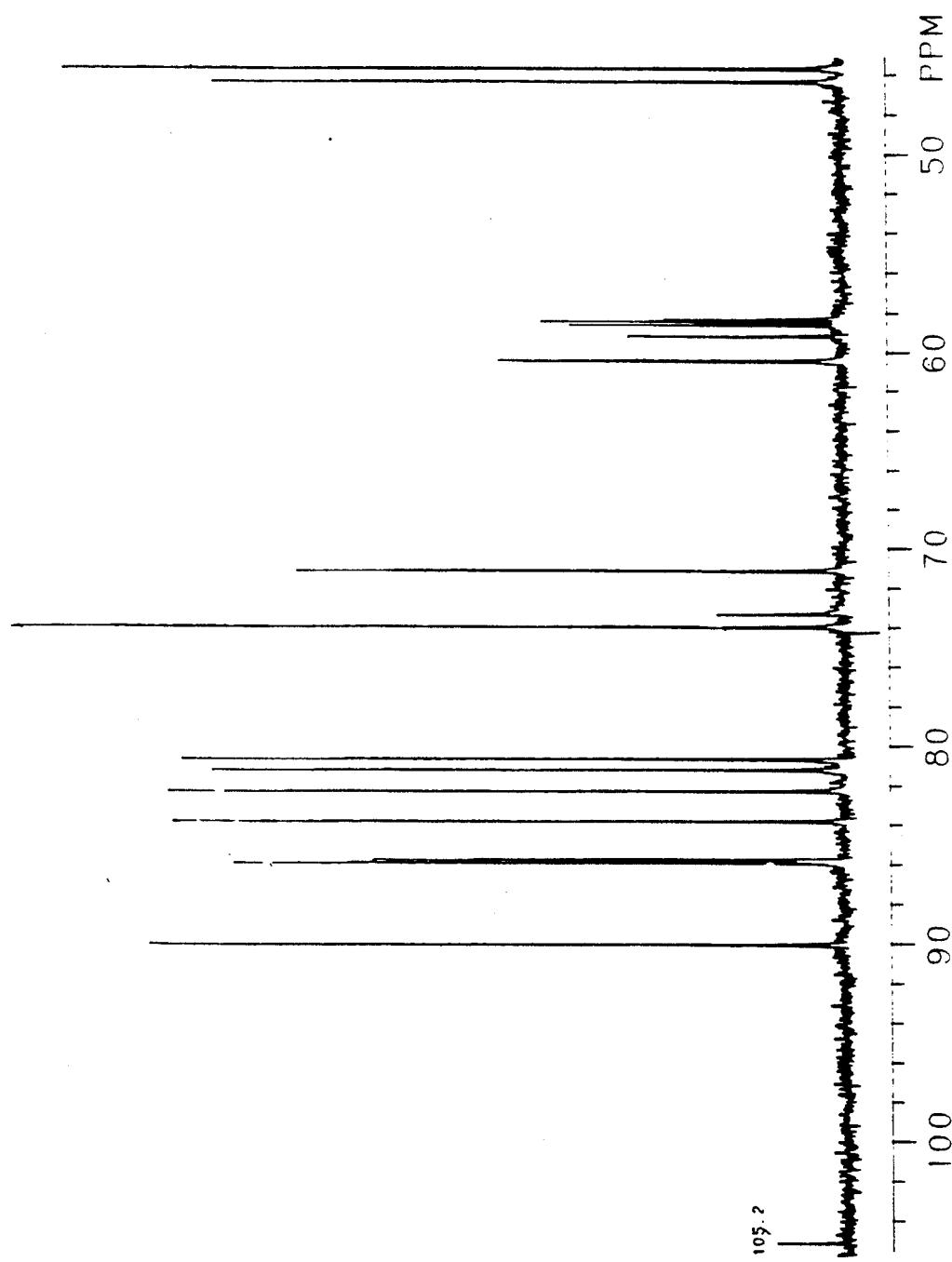
FIG. 9 is a $^{13}$C NMR spectrum of 6,6'-dichloro-6,6'-dideoxy-1',2,3,3',4,4'-hexa-O-methylsucrose synthesized by the process of the present invention.

Anal. Calc. for C$_{18}$H$_{32}$O$_9$Cl$_2$: C, 45.6; H, 6.9; O, 31.1; Cl, 15.5. Found: C, 45.7; H, 6.9; Cl, 15.2. FIGS. 8 and 9 are NMR spectra of this final product.

F. Synthesis of 6,6'-diacetoxy-1',2,3,3',4,4'-hexa-O-methylsucrose

To a suspension of cesium acetate (2.48 g, 12.95 mmol, 6. equiv.) in dry DMF (5 ml) is added the dichloride in (E) (1.0 g, 2.15 mmol in 2 ml DMF). The reaction mixture is allowed to stir at 130° C. for 24 h, then cooled to room temperature, diluted with water, and extracted with methylene chloride. The combined organic extracts are washed with water and then brine, dried over anhydrous magnesium sulfate, filtered, and concentrated in vacuo. Silica gel chromatography on a column (5 cm × 18 cm) using 50% ethyl acetate in hexanes (flow rate about 100 ml/min) provided the desired diacetate as an oil (0.98 g) in 90% yield. R$_f$ of 6,6'-diacetoxy-1',2,3,3',4,4'-hexa-O-methylsucrose in 50% ethyl acetate in hexanes is 0.29. $^1$H NMR (500.11 MHz, CD$_2$Cl$_2$) δ 2.05 (Me of acetate-6, s), 2.05 (Me of acetate-6', s), 3.03 (H-4, t, J=9.1, 9.9 Hz), 3.09 (H-2, dd, J=3.9, 9.7 Hz), 3.35 (H-1'a, d, J=10.9 Hz), 3.39 (H-3, t, J=9.1, 9.7 Hz), 3.39 (OMe-1', s), 3.42 (OMe-3', s), 3.44 (OMe-4', s), 3.47 (OMe-2, s), 3.49 (OMe-4, s), 3.53 (H-1'b, d, J=10.9 Hz), 3.56 (OMe-3, s), 3.79 (H-4', t, J=7.7 Hz), 3.91 (H-5', m, J=4.5, 6.3, 7.8 Hz), 3.97 (H-5, m, J=2.2, 4.9, 9.9 Hz), 4.01 (H-3', d, J=7.7 Hz), 4.15 (H-6a, dd, J=4.9, 11.8 Hz), 4.26 (H-6b, dd, J=2.2, 11.8 Hz), 4.26 (H-6'a, m), 4.27 (H-6'b, m), 5.47 (H-1, d, J=3.9 Hz). $^{13}$C NMR (125.76 MHz, CD$_2$Cl$_2$) δ 20.93 (Me of acetate-6'), 20.98 (Me of acetate-6), 58.56 (OMe-3'), 58.65 (OMe-4'), 58.80 (OMe-2), 59.48 (OMe-1'), 60.58 (OMe-4), 60.71 (OMe-3), 63.77 (CH$_2$-6), 65.54 (CH2-6'), 69.43 (CH-5), 74.17 (CH$_2$-1'), 78.47 (CH-5'), 79.98 (CH-4), 81.87 (CH-2), 83.45 (CH-3), 83.79 (CH-4'), 85.46 (CH-3'), 89.52 (CH-1), 104.47 (C-2'), 170.90 (CO of acetate 6'), 170.94 (CO of acetate 6).

Anal. Calc. for C$_{22}$H$_{38}$O$_{13}$:C, 51.8; H, 7.4; O, 40.8. Found: C, 51.8; H, 7.4.

G. Synthesis of 1',2,3,3',4,4'-hexa-O-methylsucrose

To a solution of diacetate as synthesized in (F) (1.08 g, 2.11 mmol) in methanol (40 ml) is added a 2M solution of sodium methoxide in methanol (8 ml) dropwise over 15 min. The pale yellow solution is stirred at room temperature for 2 h, then concentrated in vacuo, diluted with water and acidified to pH=7 by dropwise addition of 1M hydrochloric acid. The mixture is concentrated to a residue and applied directly on a silica gel column (5 cm × 15 cm) and eluted with 95% ethyl acetate:5% methylene chloride (flow rate about 100 ml/min) to provide the 1',2,3,3',4,4'-hexa-O-methylsucrose as an oil (800 mg, 90% yield). R$_f$ diol in 90% ethyl acetate in methylene chloride is 0.21, [α]$_D^{22}$=63.1 in acetone. $^1$H NMR (500.11 MHz, acetone D$_6$) δ 3.04 (H-2, dd, J=3.7, 9.6 Hz), 3.09 (H-4, t, J=9.3, 9.6 Hz), 3.34 (H-1'a, d, J=10.9 Hz), 3.36 (H-3, t, J=9.3, 9.6 Hz), 3.37 (OMe-1', s), 3.41 (OMe-4', s) 3.44 (OMe-2, s), 3.44 (OMe-3', s), 3.48 (OMe-4, s), 3.52 (OMe-3, s), 3.53 (H-1'b, d, J=10.9 Hz), 3.59 (H-6a, dd, J=4.1, 13.4 Hz), 3.63 (H-6'a, dd, J=4.5, 12.4 Hz), 3.71 (H-6b, dd, J=2.5, 13.4 Hz) 3.73 (H-6'b, dd, J=6.4, −12.4 Hz), 3.74 (H-5', m, J=4.5, 6.4, 7.7 Hz), 3.79 (H-5, m, J=2.5, 4.1, 9.6 Hz), 3.92 (H-4', t, J=7.7, 7.8 Hz), 4.00 (H-3', d, J=7.8 Hz), 5.51 (H-1, d, J=3.6 Hz). $^{13}$C NMR (125.76 MHz, acetone D$_6$) δ 58.42 (OMe-3'), 58.44 (OMe-4'), 58.66 (OMe-2), 59.41 (OMe-1'), 60.36 (OMe-4), 60.57 (OMe-3), 61.68 (CH$_2$-6'), 62.48 (CH2-6), 73.04 (CH-5), 75.02 (CH$_2$-1'), 80.00 (CH-4), 81.86 (CH-5'), 82.50 (CH-2), 82.79 (CH-4'), 84.14 (CH-3), 85.97 (CH-3'), 90.23 (CH-1), 104.50 (C-2).

Figure 10:
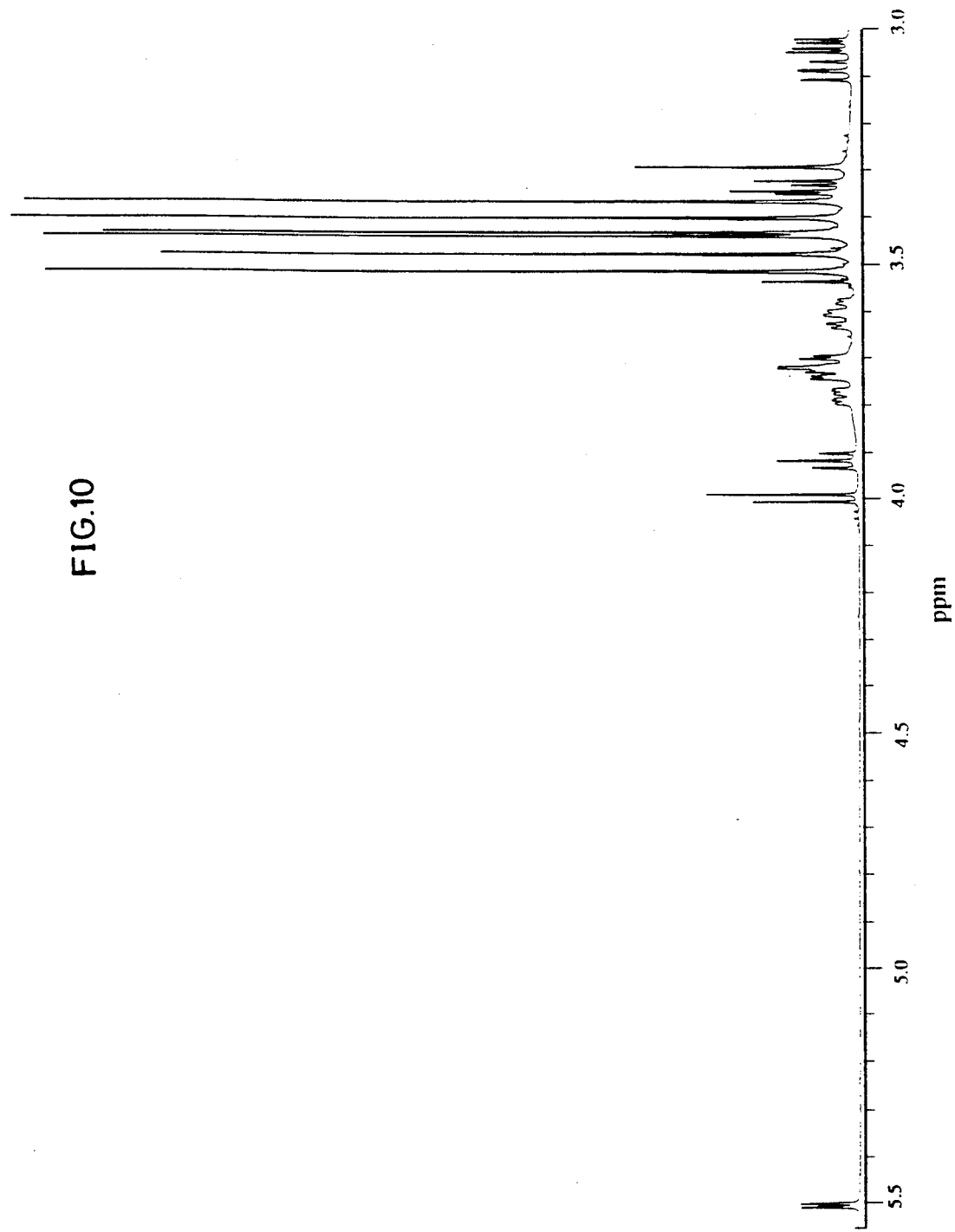
FIG. 10 is a $^1$H NMR spectrum of 1',2,3,3',4,4'-hexa-O-methylsucrose synthesized by the process of the present invention.
Figure 11:
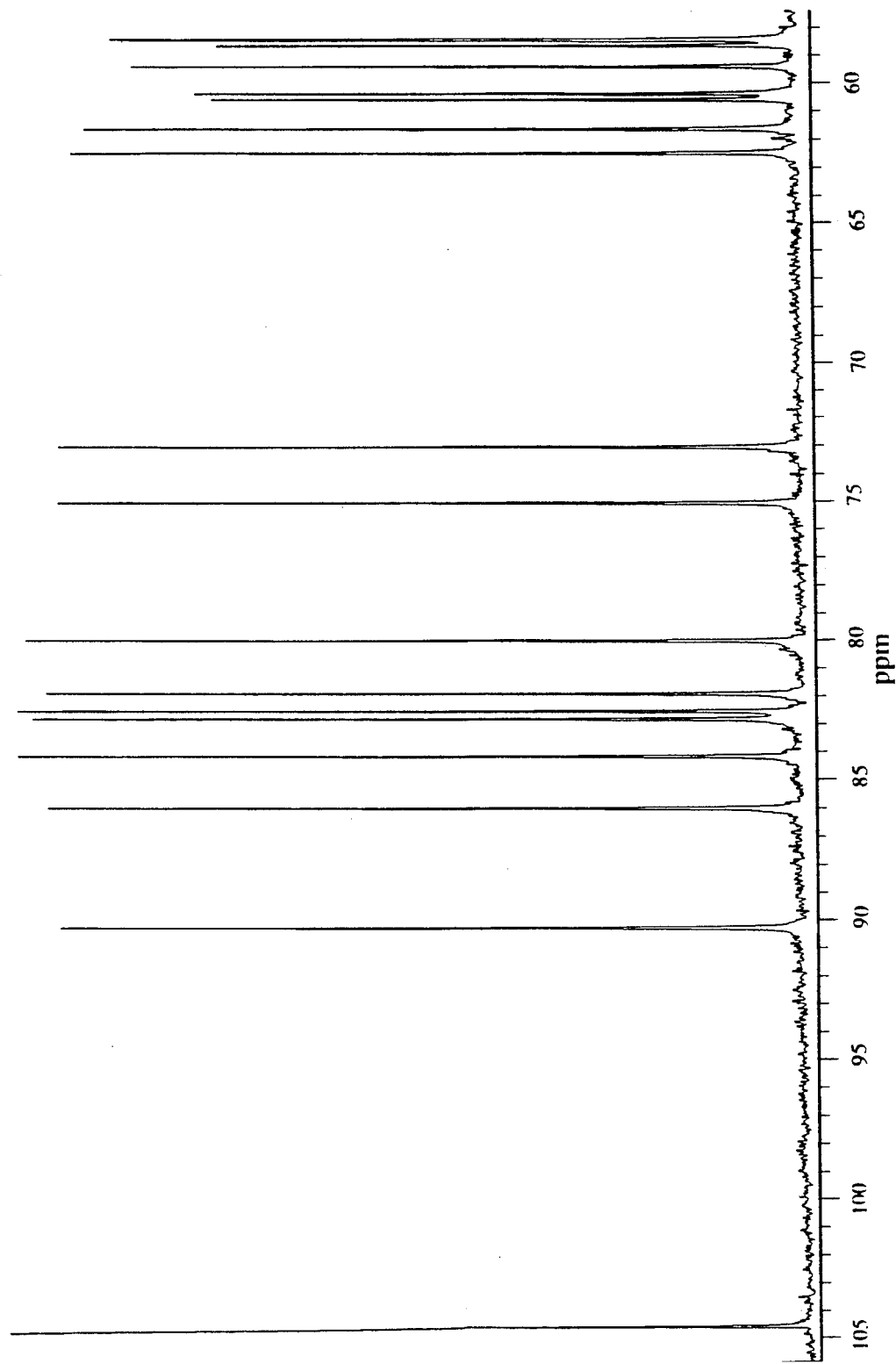
FIG. 11 is a $^{13}$C NMR spectrum of 1',2,3,3',4,4'-hexa-O-methylsucrose synthesized by the process of the present invention.

Anal. Calc. for C$_{18}$H$_{34}$O$_{11}$:C, 50.7; H, 8.0; 0, 41.3. Found: C, 50.9; H, 8.3. FIGS. 10 and 11 are NMR spectra of 1',2,3,3',4,4'-hexa-O-methylsucrose.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound having the following structure (I):

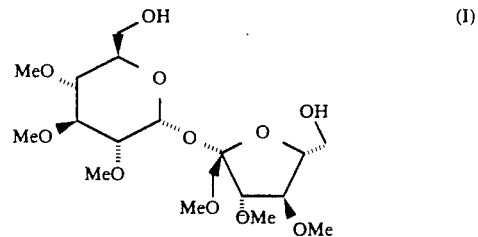

which compound is 1',2,3,3',4,4'-hexa-O-methylsucrose.

2. A process for the preparation of 1',2,3,3',4,4'-hexa-O-methylsucrose comprising the steps of:
   (a) adding 3.6 equivalents of triphenylphosphine to a solution containing between 5 mmol to 34.62 mmol of 2,3,3',4,4'-penta-O-methylsucrose to form a mixture;
   (b) adding to said mixture at a temperature between 20° C. to 28° C., 3.6 equivalents of carbon tetrachloride;
   (c) heating said mixture to a temperature of about 60° C. and stirring vigorously for a period between 60 to 75 minutes to form 6,6'-dichloro-6,6'-dideoxy-2,3,3',4,4'-penta-O-methylsucrose;
   (d) stopping the reaction in step (c) by addition of an alcohol selected from the group consisting of methanol, ethanol, and propanol and cooling the mixture to ambient temperature;
   (e) removing the alcohol from step (d) in vacuo to form a residue;
   (f) washing said residue with an aqueous hydrogen peroxide solution;
   (g) isolating 6,6'-dichloro-6,6'-dideoxy-2,3,3',4,4'-penta-O-methylsucrose;
   (h) treating said penta-O-methylsucrose compound in (g) with between 10 μl to 100 μl of boron trifluoride etherate at about −10° C.;
   (i) adding an excess of a solution of diazomethane to form 6,6'-dichloro-6,6'-dideoxy-1',2,3,3',4,4'-hexa-O-methylsucrose;
   (j) adding a suspension of 3 equivalents of cesium acetate in dimethylformamide and stirring at a temperature between 100° C. to 130° C.;

(k) isolating 6,6'-diacetoxy-1',2,3,3',4,4'-hexa-O-methylsucrose;

(l) adding an excess of 2M sodium methoxide in methanol to 6,6'-diacetoxy-1',2,3,3',4,4'-hexa-O-methylsucrose to form a solution at about 0° C.; and (m) isolating 1',2,3,3',4,4'-hexa-O-methylsucrose from said solution.

3. The process according to claim 2, wherein said alcohol is methanol.

4. The process according to claim 2, wherein said aqueous hydrogen peroxide solution in step (f) is a 10% aqueous hydrogen peroxide solution.

5. The process according to claim 2, wherein between 10 ml to 20 ml of said sodium methoxide solution is added in step (1).

6. The process according to claim 2, further comprising the step of stirring for about 2 hours the solution in step (1) after addition of said sodium methoxide and concentrating said solution in vacuo.

* * * * *